United States Patent [19]
Eckles et al.

[11] Patent Number: 5,457,320
[45] Date of Patent: Oct. 10, 1995

[54] APPARATUS AND METHOD FOR SIMULTANEOUS MEASUREMENT OF CARBON DIOXIDE AND WATER

[75] Inventors: Robert D. Eckles, Malcolm; Dayle K. McDermitt; Jonathan M. Welles, both of Lincoln, all of Nebr.

[73] Assignee: Li-Cor, Inc., Lincoln, Nebr.

[21] Appl. No.: 279,959

[22] Filed: Jul. 25, 1994

Related U.S. Application Data

[60] Division of Ser. No. 843,908, Feb. 27, 1992, Pat. No. 5,340,987, which is a continuation-in-part of Ser. No. 670,342, Mar. 15, 1991, Pat. No. 5,332,901.

[51] Int. Cl.⁶ .......................... G01N 21/35; G01N 21/05; G01N 21/61
[52] U.S. Cl. .......................... 250/345; 250/343; 356/437
[58] Field of Search .................. 250/338.5, 339.13, 250/343, 345; 356/437

[56] References Cited

U.S. PATENT DOCUMENTS 4,914,719  4/1990  Conlon et al. .................. 250/339.13
5,092,342  3/1992  Hattendorff et al. .............. 250/343 X
5,340,987  8/1994  Eckles et al. .................... 250/343 X Primary Examiner—Carolyn E. Fields
Assistant Examiner—Edward J. Glick
Attorney, Agent, or Firm—Vincent L. Carney

[57] ABSTRACT

To measure water vapor and carbon dioxide, a gas analyzer includes a light source, a reference flow cell, a sample flow cell, a detector and a source of gas. The light source, flow cells and detector are arranged so that the detector detects light transmitted from said light source through the flow cells. The flow cells have folded paths for the light. A reference signal is subtracted from a sample signal to obtain an independant variable. Carbon dioxide and air mixed with carbon dioxide are supplied as required. The carbon dioxide is supplied from a container through capillary tubes. Heat is applied to the tubes to control the flow rate. A signal representing gross concentration of the carbon dioxide as a dependant variable is obtained from said independent variable from an empirically determined polynomial.

1 Claim, 6 Drawing Sheets

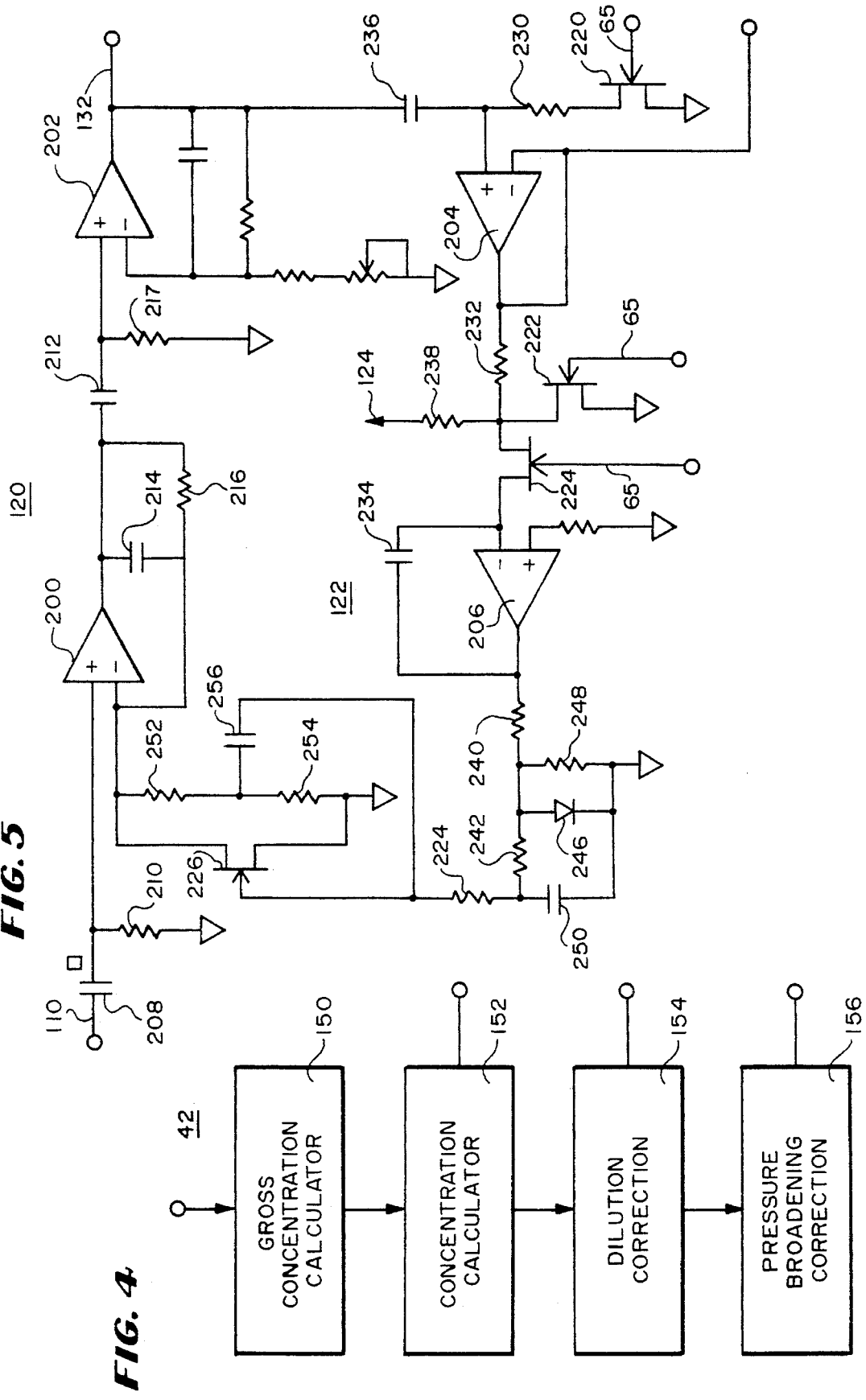

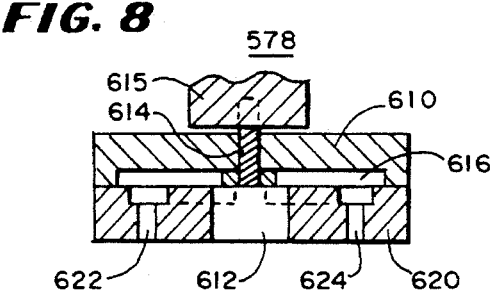
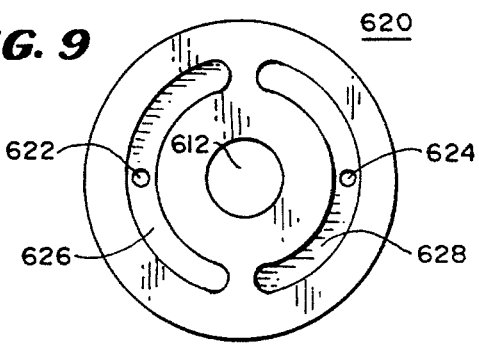
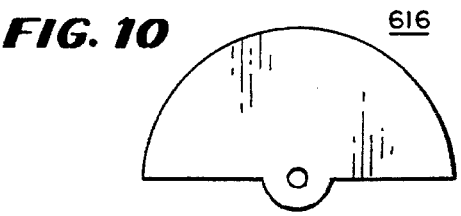
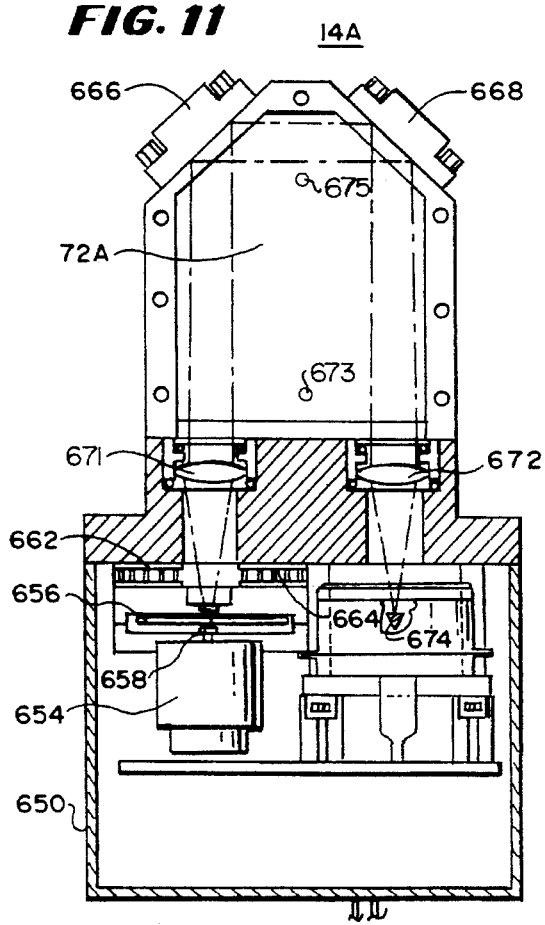
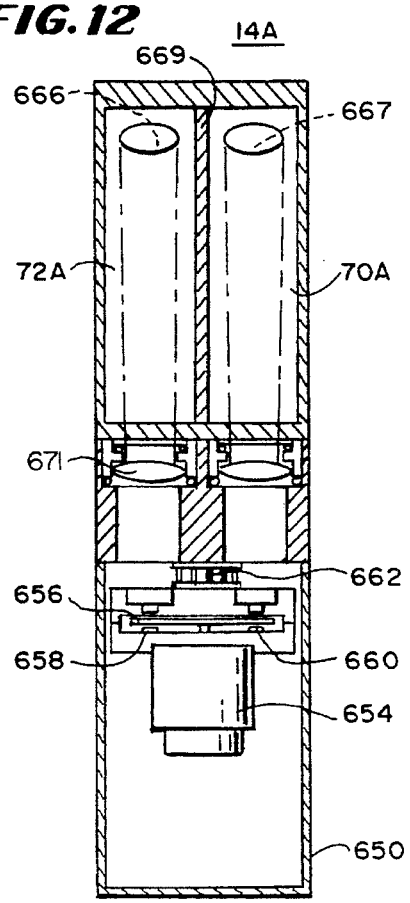

5,457,320

APPARATUS AND METHOD FOR SIMULTANEOUS MEASUREMENT OF CARBON DIOXIDE AND WATER

This application is a division of application Ser. No. 07/843,908, filed Feb. 27, 1992, now U.S. Pat. No. 5,340,987, which is a continuation-in-part application of U.S. application Ser. No. 07/670,342 filed Mar. 15, 1991, now U.S. Pat. No. 5,332,901, for Apparatus and Method For Simultaneous Measurement of Carbon Dioxide and Water in the names of Robert D. Eckles, Dayle K. McDermitt and Jonathan M. Wells.

BACKGROUND OF THE INVENTION

This invention relates to measurements of the concentration of carbon dioxide and of water vapor using infrared light.

In one class of instruments for measuring the concentration of carbon dioxide, infrared light is transmitted through a mixture of gases and the amount of infrared light in the high absorbance region of carbon dioxide that is absorbed is utilized to determine the amount of carbon dioxide that is present. In other systems, infrared light is transmitted through water vapor to determine the concentration of water vapor in accordance with the amount of infrared light that is absorbed by water vapor.

In the prior art, separate measurements have been made for water vapor and for carbon dioxide and usually these measurements have removed water vapor before measuring carbon dioxide. Moreover, in the prior art instruments, there are no corrections for measuring carbon dioxide to accomodate changes in the absorbance characteristics of carbon dioxide from secondary molecular level effects caused by the presence of some water vapor or other foreign gases. The prior art instruments did not correct for band broadening caused by second order effects of foreign gas on the gas being measured.

In one prior art carbon dioxide measuring instrument, infrared light having a center point at about 4.2 microns is transmitted through a chopper into a cell for measuring the concentration of carbon dioxide by determining the amount of infrared light in the absorbance band of carbon dioxide that is absorbed in the cell after both moisture and carbon dioxide have been removed from the gas to provide a zero reading. Next, the moisture is removed but not the carbon dioxide and the measurement is made again so that a comparison between the two readings provides a measurement of carbon dioxide related to the absorbance of infrared light. This type of prior art device is described in U.S. Pat. No. 4,803,370.

A modification of this type of device was made with the intention that it be used to measure both water vapor and carbon dioxide. An advertisement of such an instrument was circulated to some potential customers before it was built to determine pubic interest. However, it was not possible at that time to successfully build such an instrument partly because of the inability to correct errors related to second order effects of foreign gas in existing equipment.

The prior art instruments have several disadvantages such as: (1) only measuring one of carbon dioxide or water vapor at a time; or (2) not providing sufficient precision of measurements of both carbon dioxide and water vapor with infrared light passed through the mixture; (3) not using a sufficient proportion of the light from beam splitters that divide the light; and (4) not correcting for certain second order effects of foreign gases nor for self band broadening.

SUMMARY OF THE INVENTION

Accordingly, it is an object of this invention to provide a novel measuring instrument in which gases such as carbon dioxide can be measured without first removing water vapor mixed with the gas.

It is a further object of the invention to provide a novel method of measuring carbon dioxide and water vapor either separately or simultaneously while they are mixed together.

It is a further object of the invention to provide a novel method and apparatus which can simultaneously measure the concentration of water vapor and of carbon dioxide in a sample with precision.

It is a still further object of the invention to provide a novel method for correcting measurements of carbon dioxide for second order effects introduced by water vapor.

It is a further object of the invention to provide a novel method and apparatus for measuring the concentration of carbon dioxide in the presence of water vapor with precision.

It is a still further object of the invention to provide a novel measuring instrument in which different frequencies of light from a single beam of light transmitted through a mixture are used to measure the absorbants of different components of the mixture using different detectors but still exposing the light sensors with substantial light intensity.

It is a still further object of the invention to provide a novel method and apparatus for determining a relationship that may be used to derive the concentration of carbon dioxide in a mixture of gases with a relatively uncomplicated measuring instrument.

It is a still further object of the invention to provide a small, portable open-flow means for measuring gases.

In accordance with the above and further objects of the invention, an instrument transmits infrared light through a mixture of carbon dioxide and water vapor. A signal representing the amount of light absorbed in the high absorbance band of carbon dioxide is corrected by an empirically developed relationship to determine what the concentration of carbon dioxide would have been at a fixed temperature and pressure with the measured amount of light and comparison with a gas having zero carbon dioxide. This value may be further corrected for dilution, temperature difference and pressure to give more precisely the concentration of the actual sample being measured. The empirically developed relationship is a nonlinear correction determined by developing the coefficients of terms of a polynomial series of different powers utilizing experimental conditions at a given temperature and pressure.

More specifically, infrared light is radiated through both a reference gas and a gas to be measured. The signal from the reference gas is maintained constant by changing the gain of the detector amplifiers so that, if the signal transmitted through the reference gas tends to change, the amplifier corrects to maintain it the same, and doing so, changes the signal sensed from the infrared light passing through the gas sample by a scaling factor. The signal used to determine the concentration of the gas is proportional to the difference between the reference signal and the measuring signal.

In a preferred embodiment, several values are taken at a known temperature, pressure and concentration of gases. The coefficients of a polynomial representing a nonlinear curve are calculated using those known values. The coefficients are for a third order polynomial that relates the signal to gas concentration with a zero gas concentration in the reference cell. The results obtained from this calculation can be corrected for different temperatures and pressures and for measurements with either a reference gas having no carbon dioxide or to obtain a difference in the concentration of carbon dioxide between two gases. To make these corrections, the instrument includes a microprocessor in the preferred embodiment, that serves as a means for multiplying the dependent value by two ratios, one of which is the ratio of the absolute temperature of the measurements divided by the absolute temperature at which measurements were made during calibration and the other of which is the pressure at which measurements were made during calibration divided by the pressure during which measurements are being made, whereby a concentration value for zero reference concentration measurements is obtained. Unlike the prior art, this approach corrects the measurement for second order effects that change the infrared light-absorbance characteristics of carbon dioxide in the presence of foreign gases when the concentrations of those foreign gases are known.

To make simultaneous measurements, the light passing through the gases are applied to a dichroic beam splitter which reflects the frequency of light being used to measure water vapor to one sensor and transmits the frequency of light being used to measure carbon dioxide to another sensor. The beam splitter is selected to transmit a large proportion of the frequency in the absorbance band of carbon dioxide to a carbon dioxide detector and reflect a large proportion of the frequencies of light in the absorbance band of water vapor to the water vapor detector.

More specifically, a source of light having a spectrum of wavelengths including longer wavelengths and shorter wavelengths. An optical means is provided for transmitting light from said source of light through a gas sample containing a mixture of two gases, one of which has a high absorbance at said longer wavelength and the other of which has a high absorbance at said shorter wavelength. The gases in the preferred embodiment are water vapor and carbon dioxide.

A first sensor means is provided for detecting a first light within the high absorbance frequency of one of said gases and generating a first electrical signal representing said first light, and a second sensor means is provided for detecting a second light within the high absorbance frequency of the other gas and generating a second electrical signal representing said second light.

In one embodiment, a small portable unit utilizes a tank of compressed carbon dioxide. The carbon dioxide from this tank is injected into a stream of air that has had the carbon dioxide removed with sufficient precision so that the carbon dioxide and air is in precise proportion. The control of the amount of carbon dioxide is accomplished by a control circuit before the carbon dioxide is applied to the plant chamber.

In this embodiment, unscrubbed air may be applied, carbon dioxide may be applied in any proportion with the other gases after carbon dioxide has been removed or air having carbon dioxide also may be applied. To control the amount of carbon dioxide, the carbon dioxide from the tank is permitted to flow through a capillary bridge which measures the flow rate and controls it by selectively applying heat to the capillary tubes to reduce or increase flow. It is mixed with carbon-dioxide-scrubbed air in a volume tank and then pumped to a valve that proportions or selects the carbon dioxide or air treated by carbon dioxide for application to a plant chamber or to the analyzing cells. For better measurements, a folded light path may be used in one embodiment, thus permitting the light to be absorbed through a larger amount of gas.

From the above description, it can be understood that the apparatus and method of this invention has several advantages, such as: (1) it can simultaneously measure carbon dioxide and water vapor or individually measure them without separating them using a beam of infrared light passed through the mixture; (2) it can measure the difference in carbon dioxide concentrations and water vapor concentrations between two samples or with respect to zero concentration in a reference; (3) it provides precise measurements; and (4) it is relatively easy to use and economical.

SUMMARY OF THE DRAWINGS

The above noted and other features of the invention will be better understood from the following detailed description when considered with reference to the accompanying drawings in which:

FIG. 4 is a block diagram of a calibration circuit used in a portion of the embodiment of FIG. 1;

FIG. 5 is a schematic circuit diagram of a portion of the interface circuit of FIG. 3;

FIG. 8 is a sectional view of an embodiment of a valve usable in the embodiment of FIG. 7;

FIG. 9 is a plan view of a portion of the valve of FIG. 8;

FIG. 10 is a plan view of another portion of the embodiment of FIG. 8;

FIG. 11 is a sectional view of a dual-sensing cell usable for gas analysis in accordance with an embodiment of the invention; and FIG. 12 is a transverse cross-sectional view of the dual analyzing cell of FIG. 11.

DETAILED DESCRIPTION

Figure 1:
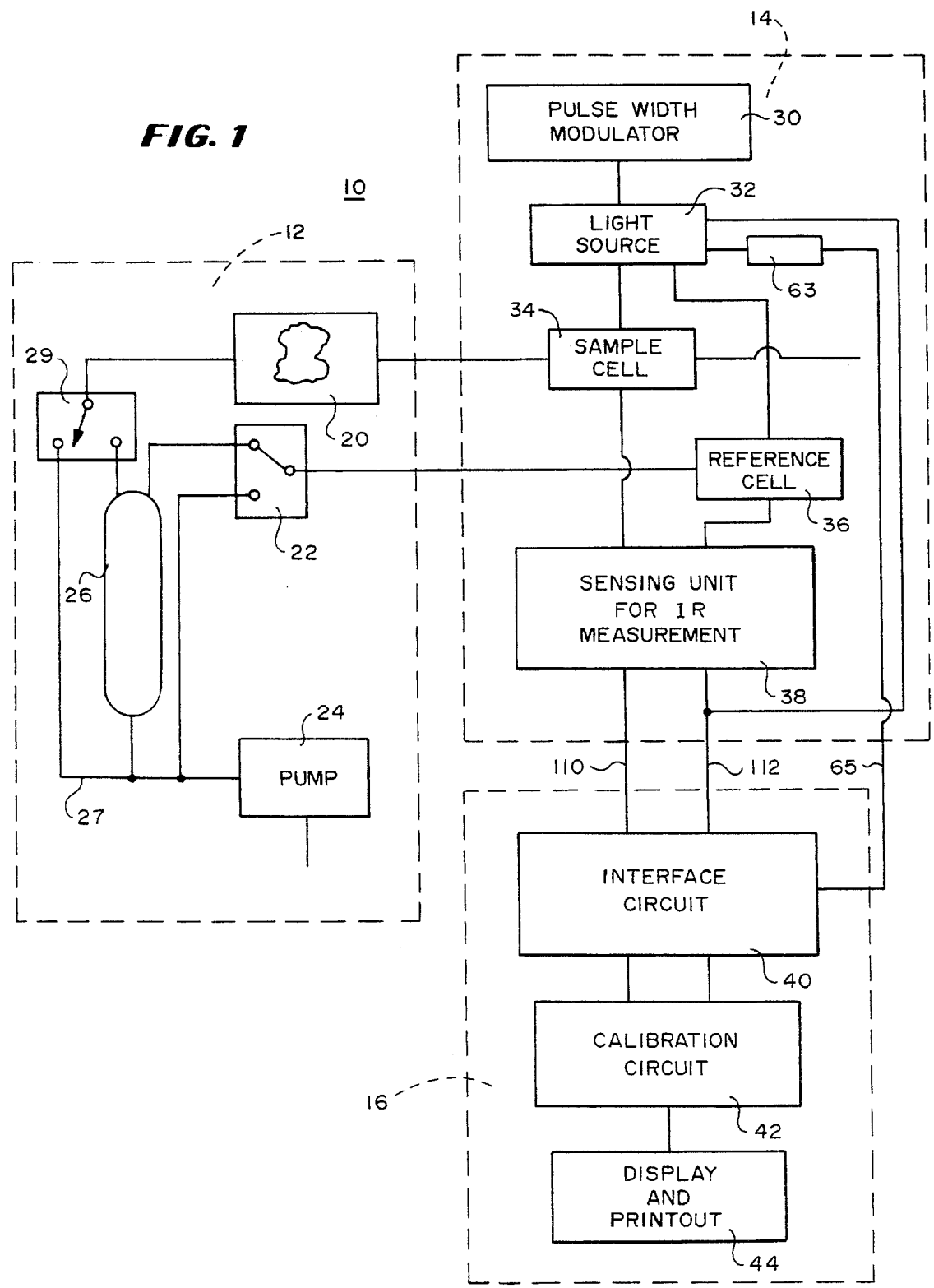
FIG. 1 is block diagram of an embodiment of the invention.

In FIG. 1, there is shown a measuring instrument 10 having a source of gas 12, a gas concentration sensor 14 and a gas concentration calculation and display circuit 16. The source of gas 12 communicates with the gas concentration sensor 14 through conduits for the flow of gas thereto and the gas concentration sensor 14 senses characteristics of the gas and transmits electrical signals to the gas concentration calculations and display circuit 16 through electrical conductors which connect the two together. The display circuit 16 displays characteristics of the gas and particularly carbon dioxide and water vapor concentrations or differences between the carbon dioxide concentration of two gases and/or differences between the water vapor concentration of two gases.

To supply gas to the gas concentration sensor 14, the gas source 12 in the preferred embodiment, which is a photosynthesis measuring instrument, includes a plant chamber 20, one or more gas valves 22, a pump 24, and a gas processing container 26. The pump 24 pumps air or another gas through the gas processing container 26 to cause it to flow through the plant chamber 20 into a sample cell and to the valve 22. The pump supplies air to the gas processing container 26 with which it communicates or with the valve 22 and a valve 29 connected to the plant chamber 20, the pump 24 and the gas processing container 26 so that the valve 22 may apply either processed gas or unprocessed gas to the gas concentration sensor 14 and the valve 29 may apply either processed gas or unprocessed gas to the plant chamber 20. The chamber 20 also communicates with the gas concentration sensor 14 to supply air thereto after the air has resided within the plant chamber 20.

In the preferred embodiment, which is a photosynthesis measuring instrument, the plant chamber is a transparent chamber of a type known in the art and briefly described in U.S. Pat. No. 4,803,370 and other patents. Such chambers may be purchased from Li-Cor, Inc., P.O. Box 4425, Lincoln, Nebr. 68504 U.S.A.

The gas processing container 26 in the preferred embodiment is a container having an inlet and outlet conduit with the appropriate chemicals between them, preferably in two compartments, one of which includes soda lime and another of which includes magnesium perchlorate so that air enters the gas processing container 26, flows through the lime which removes $CO_2$, then flows through the magnesium perchlorate to remove $H_2O$ and then flows out of the gas processing container 26.

With this arrangement, scrubbed gases such as air can be applied to the plant chamber 20 or to the gas concentration sensor to serve as a reference gas by passing the gas through the gas concentration chamber first. For that purpose, the pump 24 may pass gas through the gas concentration processor 26 into the plant chamber 20 or on the other hand, may pump gas through the valve 22 directly into the gas concentration sensor 14.

The pump 24 may pump air or be connected to pump any other gas which is desired to be used. Its outlet is connected to the inlet of the gas processing container 26 and to one inlet port of the valve 22, the other inlet port of valve 22 being connected to the outlet of the gas processing container 26. The outlet of the valve 22 is connected to the gas concentration sensor 14.

With this arrangement, the pump 24 may pump air through the gas processing container 26 and from there, scrubbed air may be applied to both the plant chamber 20 and the gas concentration sensor 14 so that gas which has been in the plant chamber 20 may be compared with gas that has not been in it. In the alternative, scrubbed gas may be applied in the same manner through the plant chamber 20 to the gas concentration sensor 14 but unprocessed air maybe passed to the gas concentration sensor for comparison therewith or some other gas such as a gas with a known concentration of carbon dioxide or water vapor. The gas source 12 is not part of this invention except insofar as it cooperates with the gas concentration sensor 14 and with the gas concentration calculating and display circuit 16.

To sense the concentration of gases applied to it from the gas source 12, the gas concentration sensor 14 includes a pulse width modulator 30, a light source 32, a sample cell 34, a reference cell 36, and a sensing unit 38. The pulse width modulator 30, the light source 32, the sample cell 34 and the reference cell 36 are generally of the type described in U.S. Pat. No. 4,803,370 and are not in themselves part of the invention except insofar as they cooperate with the other units of the gas concentration source 14.

The pulse width modulator 30 energizes the light source 32 to provide regulated constant light for sensing to the sample cell 34 and reference cell 36. A filter within the units selects infrared light which is within the absorbance spectrum of carbon dioxide and water vapor. This infrared light is absorbed by the carbon dioxide and water vapor. The source of light transmits light through band pass optical filters and has strong emission spectrums at the 4.26 micron absorption band for carbon dioxide and at the 2.59 micron absorption band for water vapor. Filters are in series with different detectors so that one detector senses the carbon dioxide absorption band at 4.26 microns and the other senses the water vapor absorption band at 2.59 microns.

A chopper wheel moving at a controlled speed applies light pulses to a sensor 63 which converts them to electrical signals and transmits the signals through cable 65 to a phase-lock loop motor control circuit and to the concentration-calculating and display system 16 to control the speed of the chopper wheel and to provide timing signals for transmitting measured values in a manner to be described hereinafter.

Light passing through the sample cell and the reference cell are sensed within the sensing unit for the respective carbon dioxide and water vapor and a signal representing the strength of the absorption band for carbon dioxide and a second signal representing the strength of the light in the absorption band of water vapor are transmitted to the gas concentration calculating and display circuit 16.

To calculate and display gas concentrations, the gas concentration calculating and display circuit 16 includes an interface circuit 40, a calibration circuit 42 and a display and printout arrangement 44. The interface circuit 40 in the preferred embodiment: (1) controls the reference signal obtained by sensing light from the reference cell; (2) subtracts the reference signal from the sample signal obtained by sensing light through the sample cell; (3) converts the signal into digital form; and (4) stores them so as to be able to process signals from measurements through the reference gas and through the sample gas, both for water vapor concentration and for carbon dioxide concentration.

However, instead of making calculations in digital form, analog circuits could be used with sample and hold provision and analog computers to provide individual signals for reference measurement and water vapor and carbon dioxide measurements for both the reference gas and the sample gas. Moreover, some calculations made by computer herein could be made by hand and constants can be separately stored in hard copy such as printing rather than in computer memory.

In the preferred embodiment, the signals for the reference values are maintained constant with an automatic gain control circuit in analog form before digitizing but could be maintained constant by digitizing first and by multiplying or dividing digital signals by a scaling value necessary to keep them constant and at the same time multiplying or dividing the sample cell measured values digitally by the same scaling factor to cause the sample cell measured values representing carbon dioxide or water vapor to vary in direct proportion to variations in the carbon dioxide and water vapor measurements of the reference gas.

The calibration circuit 42 receives the signal from the interface and develops signals representing concentration of the gases. This is accomplished by calibrating each instrument with known values in a equation representing a nonlinear polynomial which is developed individually for each analyzing instrument to provide the corrected values for one temperature and pressure. The values of concentration calculated with this polynomial can also be extended to other temperatures and pressures by another set of calculations. A determination can be made of either the difference in concentrations between the reference and the sample or the absolute concentrations if the reference has zero water vapor and zero carbon dioxide. Other corrections may be also made automatically. The instrument may separately calculate either concentration of water vapor or carbon dioxide or both and may do it simultaneously. Any suitable computer printer or display 44 may be used to display and print information. For example, a suitable printer can be obtained from Li-Cor, Inc., Lincoln, Nebr.

Figure 2:
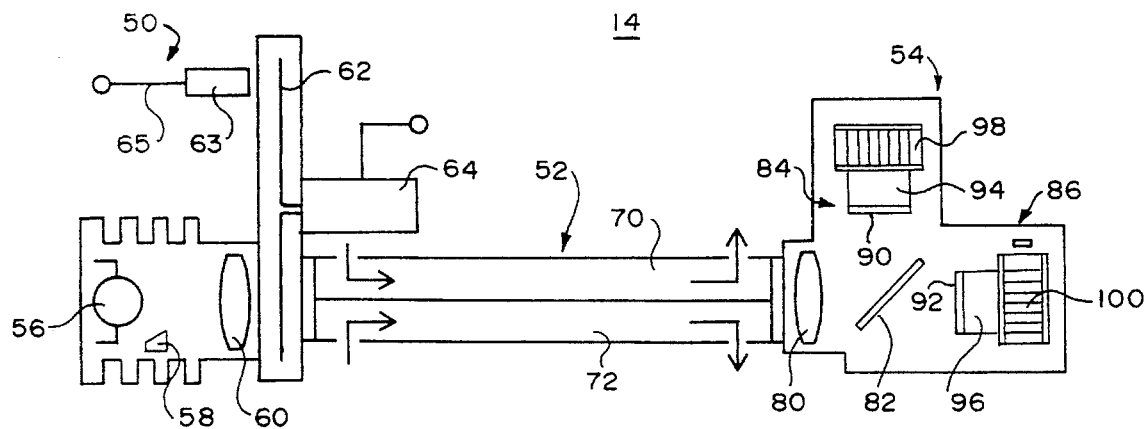
FIG. 2 is a schematic diagram of a gas concentration sensor in accordance with an embodiment of the invention.

In FIG. 2, there is shown a schematic representation of the gas concentration sensor 14 having an infrared source 50, sample and reference flow cells 52, and a photosensor section 54. The infrared source 50 generates infrared light suitable for measuring the gases which in the preferred embodiment are carbon dioxide and water vapor and transmits that light through flow cells to cause it to pass through the gas being measured and into the photosensor section 54 which measures light within the absorbance band of carbon dioxide and light within the absorbance band of water vapor. In the preferred embodiment, these measurements are made: (1) alternately between the reference gas and the sample gas; and (2) with different detectors for each gas. However, the reference and sample gas measurements could be made simultaneously through the use of additional photosensors and a single detector with replaceable filters such as on a filter wheel could be used to measure different gases in a manner to be described hereinafter.

The infrared source 50 includes a light emitting unit 56, a feedback photodiode 58, and a lens 60. The light source is energized by the pulse width modulator 30, providing more energy with a wider pulse and less energy with a shorter width pulse. The feedback photodiode 58 receives light and feeds back a signal to control the current through the light emitting unit 56 by controlling the width of the pulses from the pulse-width modulator 30 (FIG. 1). The lens 60 is a lens for focusing light from the light emitting unit 56 in a manner conventional in the art. Between the lens and the sample cell section 52, there is located a chopper shutter 62 driven by a motor 64 so as to chop the light beam before it is transmitted through the sample cell and reference cell in the sample and reference cell section 52. Its speed is maintained constant with a conventional feedback loop. A detector system 63 receives signals for the feedback loop and provides timing signals to the concentration calculating and display system 14 to distinguish between signals corresponding to reference gas measurements and sample gas measurements.

This light emitting unit is described in greater detail in U.S. Pat. No. 4,803,370, the disclosure of which is incorporated herein by reference. It is not itself part of the invention but is part of an inventive combination which cooperates together with other units to provide the precision, time economy and compactness of this invention.

The sample and reference cell section 52 includes a sample cell 70 adapted to receive the gas that is to be measured from the chamber 20 which flows therethrough and a reference cell 72 adapted to receive air through the valve 22 as a standard. The sample and reference cell are both aligned between the lens 60 and the photosensor section 54 so that light transferred from the infrared source 50 passes through both cells and into the photosensor section 54 for measurement thereof.

The photosensor section 54 includes a lens 80, a dichroic beam splitter 82, a water vapor detector assembly 84, and a carbon dioxide detector assembly 86. The lens 80 is mounted to receive light being transmitted from the infrared light source 50 through the sample cell and reference cell 70 and 72 and transmits it to the beam splitter 82. The beam splitter 82 passes light having certain wavelengths to the detector 86 and other light having other wavelengths to the detector 84.

The dichroic beam splitter 82 should transmit a high proportion of light such as at least 55 percent, having a center wavelength of 4.26 microns to the carbon dioxide detector 86 and reflect a large portion of the light having a center point of 2.4 microns, such as at least 55 percent. In the preferred embodiment, its characteristics are: (1) hardcoat; (2) transmission of more than 75 percent flat transmission band between 4.0 microns and 4.5 microns; (3) reflection of more than 75 percent between 2.45 micron to 2.70 micron; (4) optical axis 45 degrees from normal, focused radiation from point source, F equal to 3.5; (5) 0.75 inch (1.9 cm) in diameter plus or minus 0.005 inches (0.01 cm) and 0.020 inches (0.05 cm) plus or minus 0.002 inches (0.01 cm) thick; (6) environment is 0–50 degrees C. greater than 90 percent RH (relative humidity); (7) base material is synthetic sapphire; and (8) minimum optical aperture is 0.65 inch (1.65 cm) diameter. This lens is obtainable from Optical Coating Laboratories, Inc. at 2789 Northpoint Parkway, Santa Rosa, Calif. 95407-7397.

With this arrangement, the same infrared light beam is transmitted through the same paths with a mixture of air with water vapor and carbon dioxide and is sensed separately by the two photocells. A short time later, the same light passes through a reference cell with reference amounts of carbon dioxide and water vapor or no carbon dioxide and water vapor and the carbon dioxide and water vapor are each again sensed by the two different photocells.

To sense the amount of light being transmitted through the gases, the carbon dioxide sensing assembly 86 and the water vapor sensing assembly 84 each include a different one of the filters 90 and 92, a different one of the sensors 94 and 96 and a different one of thermoelectric coolers 98 and 100. The sensors 94 and 96 and thermoelectric coolers 98 and 100 are the same in the two detectors but the filters 90 and 92 differ.

To transmit light centered around 4.26 microns to the sensor 96 of the carbon dioxide sensor and block other wavelengths, the filter 92 is mounted between the beam splitter 82 and the sensor 96 and is a narrow band filter which substantially eliminates all other wavelengths of light. The filter 92 should have a center wavelength of 4.2 and have a band no wider that 150 nanometers.

In the preferred embodiment, a filter with the following characteristics is used: (1) a center wavelength of 4.27 microns plus or minus 0.5 percent; (2) a half bandwidth at 0.150 micron plus or minus 10 percent; (3) a transmission of greater than 80 percent; (4) attenuation of greater than 0.1 percent with no further blocking required; (5) substrate of synthetic Sapphire; (6) dimensions of 0.220 inches (0.56 cm) by 0.220 inches (0.56 cm) plus or minus 0.005 inches (0.1 cm) ; (7) thickness of 0.020 inches (0.05 cm); (8) edge defect of 0.020 inches (0.05 cm); (9) operating conditions down to −10 degrees centigrade, focused; and (10) focused radiation cone half angle is equal to 8 degrees, F. no. is 3.5.

Similarly, to transmit light having a wavelength centered around 2.59 nanometers, the filter 90 is mounted between the beam splitter 82 and the sensor 94 of the water vapor detector and blocks all other frequencies of light. The filter 90 should have a center wavelength of 2.5 microns and a bandwidth no greater than 100 nanometers.

In the preferred embodiment, it has the following characteristics: (1) hardcoat; (2) center wavelength 2.595 micron plus or minus 10 nm. (nanometers); (3) half bandwidth of 50 nm plus or minus 10 nm.; (4) attenuation: less than 1.0 percent transmission from 2.66 micron to 2.70 micron, less than 0.1 percent transmission greater than 2.70 micron, less than 0.1 percent transmission at wavelengths shorter than 2.44 microns; (5) blocking: none required to 6.5 micron; (6) peak transmission: greater than 60 percent; (7) optical system type: focused radiation from a point source. F. no. equal 3.5; (8) size: 0.22 in. (0.56 cm) square plus or minus 0.010 in. (0.03 cm), 0.020 in. (0.05 cm) thick, edge defect less than 0.020 inches (0.05 cm); (9) base material: synthetic sapphire; and (10) environment: minus 12 C. plus or minus 2 C., less than 90 percent RH (relative humidity).

Figure 3:
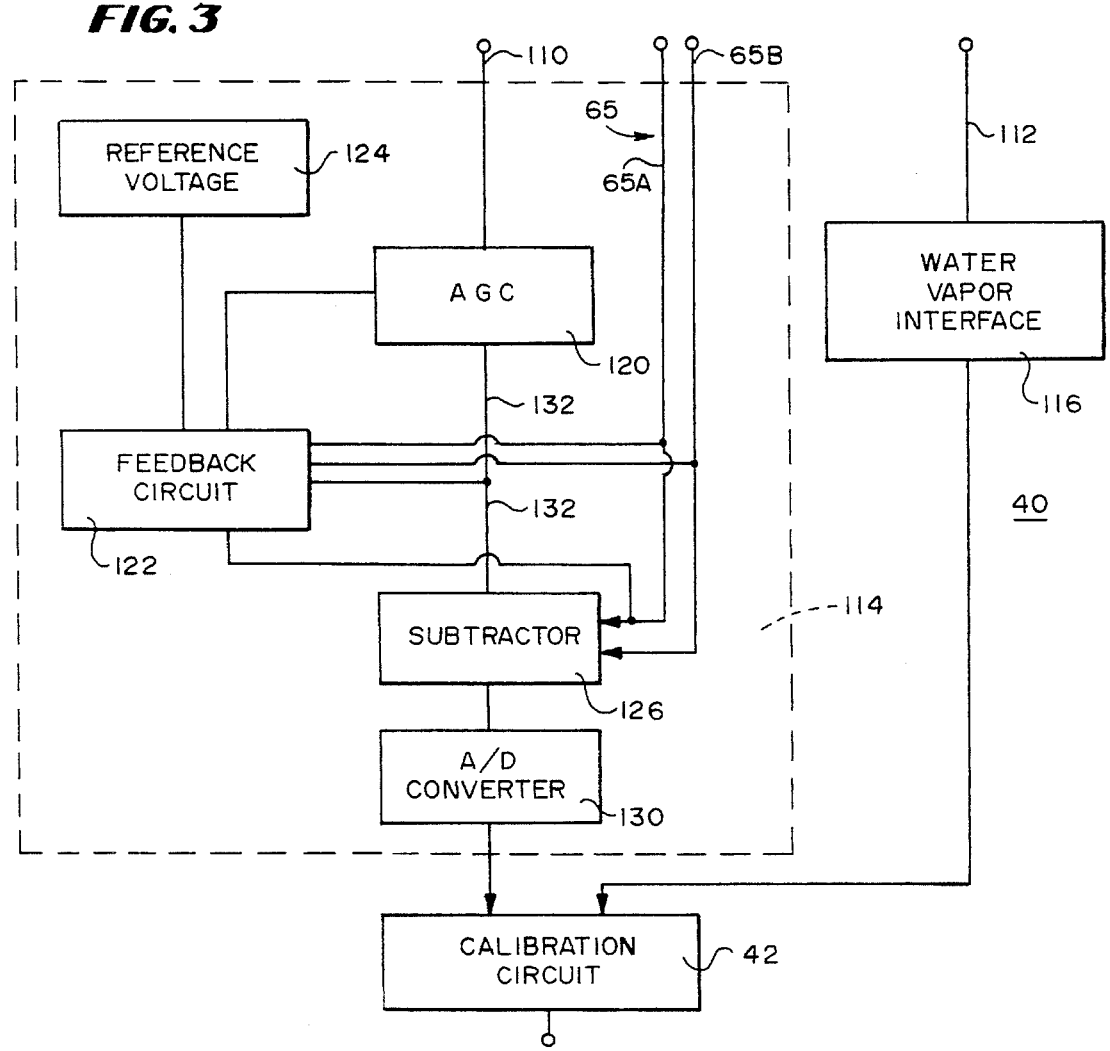
FIG. 3 is a block diagram of an interface circuit which forms a part of the embodiment of FIG. 1.

In FIG. 3., there is shown a block diagram of the interface circuit 40 having a carbon dioxide interface portion 114 and water vapor interface portion 116, each of which is electrically connected through a corresponding one of the conductors 110 and 112 to the sensing unit for infrared measurement 38 (FIG. 1). These circuits each have their outputs electrically connected to the calibration circuit 42. The carbon dioxide vapor interface portion and the water vapor interface portion 114 and 116 are substantially identical and only the carbon dioxide vapor interface 114 is shown in detail in FIG. 3 and described in detail.

To obtain a signal representing the difference between the carbon dioxide concentration in the gas sample and the carbon dioxide concentration in the reference gas, with the signal representing the carbon dioxide concentration in the reference gas being held constant, the carbon dioxide vapor interface portion 114 includes an automatic gain control amplifier 120, a feedback circuit 122, a reference voltage 124, a subtractor 126 and an analog to digital converter 130.

The signal on 110 is applied to the automatic gain control and during the time period of the reference voltage under the control of the synchronization signals from cable 65 (FIGS. 1 and 2), the feedback circuit adjusts the automatic gain control to maintain the output on conductor 132 from the output gain control constant in relation to the reference voltage 124. At the next clock indication from the cable 65 which is connected to the feedback circuit and the subtractor, the feedback circuit holds the automatic gain control constant while the signal from the sample gas is applied through the automatic gain control at the prior setting and subtracted from the reference voltage in the subtractor 126. The resulting difference signal is transmitted to the analog to digital convertor 130 for application to the calibration circuit 42, which in the preferred embodiment is a computer.

This difference signal hereinafter sometimes referred to as an independent variable is applied to the calibration circuit 42 (FIG. 1) and used to prepare a signal relating to concentration. The calibration circuit 42 performs the steps under program control for iteratively determining the constants of a polynomial, which in the preferred embodiment is a third order polynomial. This polynomial is then corrected for the appropriate temperatures and pressures during readings and used to calculate absolute concentration and differential concentrations as needed.

In FIG. 4, there is shown a block diagram illustrating the steps performed by a computer in accordance with a program described hereinafter, or in the alternative, a hardware circuit designed to make the same iterative calculations comprising a gross concentration calculator 150, a concentration calculator 152, a pressure broadening correction 156, and a dilution correction 154. The calculations performed in the calibration circuit 42 are, in the preferred embodiment, performed by a Hewlett Packard 200 computer for calibration and by an Intel 80C 188 microprocessor during operation. The calibration values a1, a2 and a3 (equation 2) are calculated by the program in table 1 on a Hewelett Packard series 200 computer but may be solved by hand in a manner known in the art. The program for calculating concentration is table 2.

$$V = K\left(1 - \frac{V_s}{V_g}\right) \qquad \text{EQUATION 1}$$

$$F(V) = a_1 V = a_2 V^2 + a_3 V^3 \qquad \text{EQUATION 2}$$

$$C = F\left(V \frac{P_0}{P}\right)\left[\frac{T+273}{T_0+273}\right] \qquad \text{EQUATION 3}$$

Both during calibration and during the operation of the analyzing unit, the reference signal for both the carbon dioxide sensor and the water Vapor sensor are held constant and a signal, V, proportional to the difference between the reference and the sample signals is obtained and converted to a digital code in the analog to digital convertor 130 (FIG. 3) of the interface circuit 40 (FIG. 1). This signal can be written as shown in equation 1 where $v_s$ is the signal from the sample gas measurement and $v_r$ is the signal from the reference gas measurement.

Since the reference signal (signal obtained from a detector in response to light transmitted through the reference gas) is held constant, it can be factored from proportionality constant k and a new constant, K, used, which constant is equal to the proportionality factor, k, multiplied by the reference signal. As the gas concentration in the sample cell increases, the sample signal (signal from a detector in response to light transmitted through the sample gas) decreases due to increased absorption of radiation. The signal output V increases in proportion to the amount of decrease of the sample signal (equation 1).

TABLE 1

Program for calibrating CO$_2$/H$_2$O analyzer

```
116   Calibration:SUB
          Calibration(Pathmu$,Filename$,Cal$,Pantry$(*))
117   !
118   ! Cal data in file → computes calibration,
          adds to 'pantry' list
119       INTEGER X,Max_Lines,Rec_Length,Dummy,
             Pantry_ptr,C
120       IF Filename$="" THEN SUBEXIT
121       ASSIGN @File TO FNFile_spec$(Pathmu$,
             Filename$);RETURN X, FORMAT ON
122       Pantry_ptr=FNHi_non_null(Pantry$(*))
123       IF NOT X THEN
124           ASSIGN @Buf TO BUFFER [FNSizeof(@File)]
125           Gen_copy(@File,@Buf)
126           Io_findsize(@Buf,Max_Lines,Rec_Length)
127           ALLOCATE Log$(1:Max_Lines) [Rec_Length]
128           Io_to_array(@Buf,Log$(*),1,Max_Lines,Dummy)
129           ASSIGN @File TO *
130           FOR C=1 TO LEN(Cal$)
131               Pantry$(Pantry_ptr+1)=FNComp_pant$(Cal$
                     [C,C],Filename$,Log$(*))
132               IF Pantry$(Pantry_ptr+1) <>""THEN Pantry
                     _ptr=Pantry_ptr+1
133               IF Pantry_ptr=SIZE(Pantry$,1)
                     THEN SUBEXIT
134           NEXT C
```

TABLE 1-continued

Program for calibrating CO$_2$/H$_2$O analyzer

```
135      ELSE
136         Ctr message("Can't access cal file. ERROR
               "&VAL$(X))
137      END IF
138   SUBEND
139   !
140   !
150   Comp_pant:DEF FNComp_pant$(Which$,Filename$,
         Log$(*), OPTIONAL Select_$)
151   !
152   ! cal date in file → puts it in array 'Log$'
153      DIM P$ [160],Search$ [20],Select$ [40]
154      REAL Vals(1:5),Vol,Highest
155      INTEGER Nvals
156      Highest=0
157      P$=""
158      Nvals=5
159      MAT Vals= (0)
160      SELECT Which$
161      CASE "M"
162         IF Filename$[1,1]="A" THEN
163            Vol=75
164         ELSE
165            Vol=FNBert_get_vg(Log$(*))
166         END IF
167         OUTPUT P$ USING "#,14A,2X,4A,X,10D,5X,6A,
               X,10D";Filename$,"VOL",Vol,"Q_",0
168      CASE "F"
169         OUTPUT Search$ USING "#,14A,2X,4A";
               Filename$,"FLOW"
170         IF NOT FNCalalready(Log$(*),Search$,P$)
               THEN
171            Cal_flow_62(Log$(*),Vals(*))
172            GOSUB Add1
173         ELSE
174            RETURN P$
175         END IF
176      CASE "W"
177         OUTPUT Search$ USING"#,14A,2X,4A";
               Filename$, "H2O"
178         IF NOT FNCalalready(Log$(*),Search$,P$)
               THEN
179            IF NPAR=4 THEN Select$=Select_$
180            Cal_xxx_62(Log$(*),"H2O",Vals(*),
               Select$,Highest) water cal
181            GOSUB Add1
182         ELSE
183            RETURN P$
184         END IF
185      CASE "C"
186         Select$=""
187         OUTPUT Search$ USING "#,14A,2X,4A";
               Filename$,"CO2"
188         GOSUB Co2
189      CASE "H"
190         Select$="1 IN 0 1000,"
191         OUTPUT Search$ USING "#,14A,2X,4A";
               Filename$,"CO2H"
192         GOSUB Co2
193      CASE "L"
194         Select$="1 OUT 50 900,"
195         OUTPUT Search$ USING "#,14A,2X,4A";
               Filename$, "CO2L"
196         GOSUB Co2
197      END SELECT
198      RETURN P$&" ["&Select$&"] {"&VAL$ (Highest)
               &"} "
199   Co2:IF NOT FNCalalready(Log$(*),Search$,P$)
               THEN
200         Code$="CO2/1"
201         IF Filename$[1,1]="A" THEN
202            Code$="CO2/0"
203            Select$[LEN(Select$)+1 ="4 IN 35 45,"
204         END IF
205         IF NPAR=4 THEN Select$[LEN(Select$)+1]=
               Select_$
206         Cal_xxx_62(Log$(*),Code$,Vals(*),Select$,
               Highest) CO2 Cal
207         GOSUB Add1
208      ELSE
209         RETURN P$
201      END IF
211      RETURN
212   Add1: IF SUM(Vals) <> THEN
213         OUTPUT P$ USING "#,20A,"&VAL$(Nvals)&"
               (X,MD.3DE)";Search$,Vals(*)
214      END IF
215      RETURN
216   FNEND
217   !
218   !
220   Cal_xxx_62:SUB Cal_xxx62(Log$(*),Code$Co2cal(*),
         Select$,Highest)
221   !
222   ! code can be H20, CO2/0, CO2/1, CO2/2
223      REAL Co2_cal_coeff(1:4),T1,T2,Thi,Tlo,
         K_coeff (1:2)
224      INTEGER Num_co2,I,Num_cuts,Dummy,Hirange
225      DIM True(1:50),Mv(1:50),Temp(1:50),Abs(1:50)
228      Dummy=FNGet_records(Code$,Log$(*),Select$,
         4,Temp(*),1,True(*),2,Mv(*),5,Abs(*))
         ! select relevant measurements to use
231      IF Dummy=0 THEN ! quit if none
232         MAT Co2cal= (O)
233         SUBEXIT
234      END IF
235      Num_co2=Dummy
237      Condition(True(*),Mv(*),Num_co2,Temp(*),
         Abs(*)) ! correct for zero shift
238      Highest=MAX(True(*))
239      ALLOCATE REAL K(1:Num_co2)
240      Avk=O
241      Nk=O
242      IF Code$ <> CO2/O" THEN
243         FOR I=1 TO Num_co2 ! find average
               absorption voltage, for K factor
244            IF True(I)=O THEN
245               Avk=Avk+Abs(I)
246               Nk=Nk+1
247            END IF
248         NEXT I
249         IF Nk THEN Avk=Avk/Nk
250      END IF
251      Co2cal(1)=SUM(temp)/Num_co2
252      FOR I=1 TO Num_co2 ! adjust concentrations
               for temperature
253         True(I)=True(I)*(Co2cal(1)+273)/(Temp(I)
               +273)
254         IF Avk THEN K(I) = (1-Abs(I)/Avk)
255      NEXT I
256         Linear_regress(Mv(*),True(*),Co2_cal_
               coeff(*),Num_co2,3) ! find
               coefficient of best fit
257      IF Nk THEN
258         Linear_regress(Mv(*),K(*),K_coeff(*),
               Num_co2,1) ! find K factor
259         Co2cal (2)+1.0/K_coeff(2)
260      ELSE
261         Co2cal(2)=0
262      END IF
263      Co2cal(3)=Co2_cal_coeff(2)
264      Co2cal(4)=Co2_cal_coeff(3)
265      Co2cal(5)=Co2_cal_coeff(4)
267   SUBEND
268   !
269   !
270   Linear_regress:SUB Linear_regress(Xdata(*),
         Ydata(*),Aa(*),INTEGER Number,Power)
271   ! rev 0 10/1/84
272   ! Linear regression
273      OPTION BASE 1
274      INTEGER I,J
275      ALLOCATE Xx(Number,Power+1),Xtmp(Power+1,
         Number),Prodx(Power+1,Power+1),
```

TABLE 1-continued

Program for calibrating $CO_2/H_2O$ analyzer

```
                 Xtrn(Power+1,Number),Z(Number)
276         FOR I-1 TO Number
277              Z(I)=Ydata(I)
278              FOR J=1 TO Power+1
279                   Xx(I,J)=Xdata(I)^(J-1)
280              NEXT J
281         NEXT I
282         MAT Xtrn+ TRN(Xx)
283         MAT Prodx= Xtrn*Xx
284         MAT Prodx= INV(Prodx)
285         MAT Xtrnp= Prodx*Xtrn
286         MAT Aa= Xtrnp*Z
287    SUBEND
288    !
289    !
290    Condition:SUB Condition(True(*),Mv(*), INTEGER
                 N, OPTIONAL A(*),B(*),C(*))
291         !
292         !adjust voltages for zero drift
293         INTEGER I, Nz
294         REAL Offset
295         REDIM True (1:N),Mv(1:N)
296         IF N<2 THEN SUBEXIT
297         IF NPAR>=4 THEN REDIM A(1:N)
298         IF NPAR>=5 THEN REDIM B(1:N)
299         IF NPAR>=6 THEN REDIM C(1:N)
300         ALLOCATE INTEGER Subs(1:N)
301         MAT SORT True TO Subs
302         Nz=0
303         Offset=0
304         FOR I=1 TO N
305              IF True(Subs(1))=0 THEN
306                   Nz=Nz+1
307                   Offset=Offset+Mv(Subs(1))
308              END IF
309         NEXT I
310         IF Nz THEN
311              Offset=Offset/Nz
312              MAT Mv= Mv-(Offset)
313         END IF
314         MAT REORDER True BY Subs
315         MAT REORDER Mv BY Subs
316         IF NPAR>=4 THEN MAT REORDER A BY Subs
317         IF NPAR>=5 THEN MAT REORDER B BY Subs
318         IF NPAR>=6 THEN MAT REORDER C BY Subs
319    SUBEND
320    !
321    !
```

TABLE 2

```
              42
0 \S
              43
0 \ Intermediate Computations 880901EDP,891222BDD
1   EXIT
2   FVARIABLE _IC1
3   : .IntCmp1 Fetch _IC1 F. ;
4        {IC1} DCONSTANT IntCmp1>
5   FVARIABLE _IC2
6   : .IntCmp2 Fetch _IC2 F. ;
7        {IC2} DCONSTANT IntCmp2>
9   FVARIABLE _IC3
9   : .IntCmp3 Fetch _IC3 F. ;
10       {IC3} DCONSTANT IntCmp3>
11  EXIT
              44
0 \ Misc Computations 880901EDP,891227BDD
1   Float .610828485594 FCONSTANT doA
2   Float 242.624430064 FCONSTANT doB
3   Float 7.64477566393 FCONSTANT doC
4   : DewPt ( KPa -- ) Fetch ?System IF FDUP
5        dpA F/ LOG FDUP doB F* FSWAP doC
         FSWAP F-F/
6        Store DewPtC THEN FDROP ;
7   Float .4428 F CONSTANT vc1 \
             Vapor correction values
8   Float 1.9479 FCONSTANT vc2 \
             For CO2 um/m calculation
9   Float 0.002202 FCONSTANT vc3 \
10  : vcAdj ( um/m -- um/m' ) 1.0 FOVER vc3 F*
             vc2 F+ F/ vc_1 F+
11       Fetch H2kPa GetP(kPa) F/ F* 1.0 F+ F* ;
12  EXIT
              45
0 \ Misc Computations 880901EDP,891226BDD
1   Float 18.0 FCONSTANT 18.0
2   Float 29.0 FCONSTANT 29.0
3   EXIT
              48
0 \ Misc Computations 880901EDP,900206BDD
1   : kPa (m/m -- kPa ) GetP (kPa) F* ;
2   : X(y) ( e/p -- FL ) Fetch ?Vapor
3        IF aCAL bCAL F- F* 1.0 F+ bCAL F*
4        ELSE FDROP 1.0 THEN ;
5   : TempAbs ( T -- T' )
6        (TempAbsolute) F+ TCAL (TempAbsolute) F+ F/;
7   : Milli ( FL -- FL' ) 1000.0 F/ ;
8   : MolWtAir ( m/m -- ) Milli 1.0 FOVER F-29.0 F*
9        FSWAP 18.0 F* F+ Store MWA ;
10  : (gm) ( m/m -- g/g ) Fetch MWA F/ 18.0 F*
             1000.0 F* ;
11  EXIT
              49
0 \ Misc Computations 880901EDP,891207BDD
1   : (H2data) ( m/m -- )
2   Fetch ?System 0= Fetch ?Vapor 0=AND
3   IF FDROP 0.0 Store H2m/m 0.0 Store>H2m/m
4        0.0 Store H2kPa 0.0 Store H2g/g
             0.0 Store>H2kPa
5        0.0 Store>H2g/g 29.0 Store MWA
6   ELSE FDUP Store H2m/m FDUP MolWtAir \Absolute
7        FDUP Fetch H2Ref F- FDUP Store>H2m/m\
             Differential
8        FSWAP
9        \ Absolute Computations
10       Milli FDUP kPa FDUP Store H2kPa DewPt (gm)
             Store H2g/g
11       \ Differential Computations
12       Milli FDUP kPa Store >H2kPa (gm)
             Store>H2g/g THEN ;
13  EXIT
              50
0 \ Misc Computations 880901EDP,900308BDD
1   Float 44.0 FCONSTANT 44.0
2   : (ubar) ( ppm -- ubar ) GetP(kPa) F* 1000.0 F/;
3   : (ugm) ( ppm-up/g ) Fetch MWA F/ 44.0 F* ;
4   : JMWVaporTwiddle ( um/m -- um/m' ) Fetch ?Vapor
             2 = IF
5        1000.0 Fetch H2Ref F- 1000.0 Fetch H2m/m F-
             F* THEN ;
6   : (C2data) ( ppm -- ) JMWVaporTwiddle
7        FDUP Store C2um/m \ Absolute
8        FDUP Fetch C2Ref F- FDUP Store>C2um/m \
             Differential
9        FSWAP
10       FDUP (ubar) Store C2ubar (ugm) Store C2ug/g
11       FDUP (ubar) Store>C2ubar (ugm) Store>C2ug/g ;
12  EXIT
              51
0 \S
              52
0 \ F(x), F'(x), FInverse(x) 891211BDD
1   : F(x) ( X -- X' ) FDUP FDUP
2        CCAL F* BCAL F+ F* ACAL F+ F* ;
3   : (F'(x) ( X -- X' ) FDUP
4        CCAL 3.0 F* F* BCAL 2.0 F* F+ F* ACAL F+;
5   Float 0.5 FCONSTANT Tolerance
6   : FInverse(x,mv) ( Ref mv0 -- mv ) FSWAP FNEGATE
             FSWAP
7        0.0 FSWAP
8        BEGIN FSWAP FOVER F- FABS Tolerance F <
             NOT WHILE
9        FOVER FOVER F(x) F+ FOVER F' (x) F/
```

TABLE 2-continued

```
10         FOVER FSWAP F– REPEAT FNIP ;
11  EXIT
              53
 0  \S Calibration 890510EDP,891207BDD
 1  : H2AdjmV ( mv -- adjmV ) GetPCAL F* ;
 2  : C2AdjmV ( mv -- adjmV )
 3       Fetch H2m/m Milli X(e/p) F/ H2AdjmV ;
 4  EXIT
              54
 0  \H2O based on a dew point hygrometer for 6252
       only 890510EDP
 1      \ 891218BDD
 2  \Lowes constants
 3  Float 6.1078 FCONSTANT Lowe0        \A0
 4  Float 4.4365E-1 FCONSTANT Lowe1     \A1
 5  Float 1.4289E-2 FCONSTANT Lowe2     \A2
 6  Float 2.6505E-4 FCONSTANT Lowe3     \A3
 7  Float 3.0312E-6 FCONSTANT Lowe4     \A4
 8  Float 2.0341E-8 FCONSTANT Lowe5     \A5
 9  Float 6.1368E-11 FCONSTANT Lowe6    \A6
10  : Lowes (T -- e) FDUP Lowe6 F* Lowe5 F+
       FOVER F* Lowe4 F+
11       FOVER F* Lowe3 F+ FOVER F* Lowe2 F+
       FOVER F* Lowe1 F+ F*
12       Lowe0 F+ ;
13  : f(mV) ( mV -- T ) F(x) KCAL F+ ;
14  EXIT
              55
 0  \ Calibration 880901EDP,900214BDD
 1  Global
 2  : H2data ( Mv -- ) SetH2
 3       Fetch ?System ( Get System Type )
 4       IF ( 6262 BDD )
 5       Fetch H2Ref Fetch TC
              TempAbs F/                    \(1)
 6            mVCAL FInverse(x,mv) GetPCAL
              F/                            \(2)
 7            1.0 FOVER KCAL F/ F-          \(3)
 8            FROT F* F+                    \(4)
 9            GetPCAL F* F(x) Fetch TC
              TempAbs F*                    \(5)
10       ELSE ( 6252 ) f(mV)
11            Fetch ?Vapor IF FDUP Store DewPtC
              THEN Lowes
12            GetP(kPa) F/ 100.0 F* THEN
13       (H2data) ;
14  Local
```

The calibration of the analyzer consists of measuring the output V (hereinafter sometimes referred to as the independent variable) at several gas concentrations, and mathematically determining the coefficients for a third order polynomial F(V) that relates V to gas concentration, with a zero gas concentration in the reference cell as shown in equation 2. Coefficients $a_1$, $a_2$, and $a_3$ are manufacturer-determined for the specific instrument and are unique to each analyzer. The calibration function F(V) (hereinafter sometimes referred to as the dependent variable) is only valid for the temperature and pressure at which it was determined and a zero gas concentration in the reference cell.

It has been found empirically that absolute temperature affects the gas concentration in a linear fashion, while pressure affects the signal output, V, in a linear fashion. Therefore, the expression relating signal output to gas concentration with a zero gas concentration in the reference cell (absolute mode) is as shown in equation 3. The computer adjusts the dependent value by multipying it by the factors of equation three. The temperature, T, and pressure, P, are measured and inserted into the computer for this purpose. The corresponding temperatures and pressures during calibration are indicated by $T_o$ and $P_o$. Except at high altitudes, the effects of pressure can be compensated by adjusting the gain of the analyzer.

With some other concentration in the reference cell, the gain of the detector is higher because the analyzer seeks to maintain the reference signal at a constant level. The increased gain means that the function F(V) should now be steeper since the analyzer is now more sensitive.

If we know the calibration function F(V) and the reference concentration in the reference cell, we can predict the factor G by which the gain has changed. If the detector output at the reference concentration is what the detector's output would be with reference concentration in the sample cell and zero concentration in the reference cell, then from equation 1, equation 4 can be derived where the reference signal, $V_{sr}$, is the signal output that would exist if there were zero concentration in the reference cell and reference concentration in the sample cell. The reference signal is given by the inverse of F(V), corrected for temperature and pressure as shown by equation 5.

$$G = \frac{V_{ST}}{V_g} = \left(1 - \frac{V_T}{K}\right) \qquad \text{EQUATION 4}$$

$$V_g = F^{-1}\left(C_g\left[\frac{T_0 + 273}{T + 273}\right]\right)\left(\frac{P}{P_o}\right) \qquad \text{EQUATION 5}$$

$$C = F\left[(VG + V_T)\frac{P_0}{P}\right]\left[\frac{T + 273}{T_0 + 273}\right] \qquad \text{EQUATION 6}$$

The general expression for gas concentration C in the sample cell given reference concentration in the reference cell and analyzer signal output V is shown in equation 6. The C is simply C– reference concentration as shown in equation 7.

The number of mole fractions of carbon dioxide c, (micromole/mole), comes directly from equation 6. The reference concentration value (micromole/mole), reflects the effects of dilution by water vapor, if it is not dry. Carbon dioxide differential umol/mol is c– the reference concentration. Carbon dioxide partial pressure, Pc, is computed from c and total pressure P (kPa) by equation 8. The carbon dioxide weight fraction (microgram/gram) is computed as shown in equation 9.

The mole fraction of water vapor w (millimole/mole) is computed from equation 6. Differential water vapor (millimole/mole) is w minus the reference mole fraction (millimole/mole). Vapor pressure e (kPa) is computed from the water vapor mole fraction w and total pressure P (kPa) as shown by equation 10. The abbreviations umol/mol, mmol/mol, and ug means micromole per mole, millimole per mole and microgram respectively.

The dewpoint temperature (degrees Celsius) is computed from an equation that was fit to the data of Goff and Gratch (1946), Trans. Amer. Soc. Heat. and Vent. Eng., Vol. 52, p. 95, as given by List (1966), *Smithsonian Meterological Tables*, 6th rev.

$$\Delta C = F\left[(VG + V_g)\frac{P_0}{P}\right]\left[\frac{T + 273}{T_0 + 273}\right] - C_T \qquad \text{EQUATION 7}$$

$$p_c = \frac{cP}{1000} \qquad \text{EQUATION 8}$$

$$C_g = \frac{44c}{M} \qquad \text{EQUATION 9}$$

$$e = \frac{wP}{1000} \qquad \text{EQUATION 10}$$

$$T_d = \frac{242.62z}{7.6448 - z}$$ EQUATION 11 where $z = \log_{10}\left(\frac{e}{.61083}\right)$ and $e$ is vapor pressure in kPa.

$$w_g = \frac{18w}{1000M}$$ EQUATION 12 ed. The Smithsonian Institution, 527 pp. These tables gave saturation vapor pressure as a function of temperature over a range of −50 to 50 degrees Celsius as shown in equation 11. The water vapor weight fraction (mg/g) is shown by equation 12 where M is given after equation 9 is calculated.

Water vapor can influence infrared detection of carbon dioxide in three ways: (1) direct absorption in the carbon dioxide waveband of interest; (2) dilution; and (3) pressure broadening. Direct infrared absorption by water vapor can be virtually eliminated by judicious choice of wavebands and filters, and methods to correct for dilution are well known; however, pressure broadening is more of a problem.

Gas phase absorption of infrared radiation is due to energy-induced changes in vibrational and rotational energy states. Such energy states are altered by intermolecular collisions which increase in number as pressure increases. The kinetic theory of gases and quantum mechanics predict that absorption band widths increase with pressure and it is observed that broad band infrared absorption increases as pressure increases at constant absorber concentration.

Not all gases are equally effective in causing pressure-induced line broadening. Gases that are similar are more effective than dissimilar gases. This effect is embodied in the concept of equivalent pressure or effective pressure. Total pressure P is equal to the sum of partial pressures of component gases, while equivalent pressure is defined as shown in equation 13 where $a_1$ and $a_2$, etc are weighing factors representing the pressure broadening effectiveness of each gas species relative to nitrogen as shown in equation 14 and carbon dioxide in nitrogen as shown in equation 15.

In a simple atmosphere made up of water vapor with pressure e, plus dry gases with pressure P, so that as shown in equation 16, or, in mole fraction units as shown in equation 17, where $X_d$ is the mole fraction of all dry gases and $X_w$ is the water vapor mole fraction (e/P), the equivalent pressure is as shown in equation 18. In principle, the effective pressure varies with carbon dioxide partial pressure but the carbon dioxide partial pressure is so small that it can be neglected. Thus, if other atmospheric components are constant, an equivalent $P_c = a_1 p_1 + a_2 p_2 + \ldots$ EQUATION 13

$(a_{N_2} = 1)$ EQUATION 14

$P_c = P_{N_2} + 1.3\, P_{CO_2}\ (2)$ EQUATION 15

$P = P_d + e$ EQUATION 16

$1 = X_d + X_w$ EQUATION 17

$P_c = \Sigma a_i p_i + a_w e$ EQUATION 18 pressure can be defined as shown in equation 13 where dry gases with pressure P, is the total pressure of dry air, and $a_d$ is a dry air weighting factor. Preferably, the analyzers are calibrated using carbon dioxide or water vapor in air so a dry air weighting factor equal to 1 is taken as the standard condition. Substituting equation 17 into equation 19 gives equation 20.

The value of $a_w$ is not an intrinsic constant comparable to other such values in the literature because it uses dry air as a reference instead of nitrogen. Its value has been empirically determined to be about 1.5 against dry air. Equation 20 can be extended to include nitrogen as standard, and both water vapor and oxygen (or other gases) as variable components. Effective pressure can be written in a more general form to anticipate that possibility as shown in equation 21. Equation 20 can be compactly rewritten as shown in equation 22 where equation 23 is true and then incorporated into the carbon dioxide calibration function.

The form of the carbon dioxide calibration function (equation 3) was derived empirically, but it can also be derived from a "scaling law" call the "nonoverlapping line approximation" which holds when $P_c = a_d P_d + a_w e = P(a_d X_d + a_w X_w)$ EQUATION 19

$P_c = P[1 + (a_w - 1)X_w]$ EQUATION 20

$P_c = P[1 + (a_w - 1)X_w + \Sigma(b_i - 1)X_i]$ EQUATION 21

$P_c = P\chi(X_w)$ EQUATION 22

$\chi(X_w) = 1 + (a_w - 1)X_w$ EQUATION 23

EQUATION 24

$$V_T = \chi(w_T)F^{-1}\left(\frac{cT}{\chi(w_T)}\left[\frac{T_0 + 273}{T + 273}\right]\right)\frac{P}{P_0}$$

$$G = 1 - \frac{V_T}{K}$$

$$C = \chi(w_g)F\left(\frac{VG + V_T}{\chi(w_g)}\ \frac{P_0}{P}\right)\frac{T + 273}{T_0 + 273}$$

$$\Delta c = c - c_T$$

absorber concentrations are low or pathlengths are short. If effective pressure from equation 22 is substituted for P in that derivation, the results gives carbon dioxide mole fraction corrected for pressure broadening due to the presence of water vapor. The calibration equations for carbon dioxide then become as shown in equation 24. The water correction is based upon a theoretically justifiable procedure which requires determination of a single physically meaningful constant.

A dilution correction can be applied, if desired. When one component gas of multicomponent mixture is decreased at constant pressure, the partial pressures of all other components are increased accordingly. For example, if water vapor is removed at constant pressure, then the partial pressures of other components increase according to equation 25 where w is the water vapor mole fraction (millimole/mole) and the $p_i$ wet are partial pressures of other component gases before water vapor was removed. For individual components, equation 25 becomes equation 26. If water vapor is added to or removed from $$P = \frac{\Sigma p_i^{wet}}{(1 - w/1000)}$$ EQUATION 25

$$p_i^{dry} = \frac{p_i^{wet}}{(1 - w/1000)}$$ EQUATION 26

-continued $$C_S^{WT} = C_S^{WS} \frac{(1 - w_{ref}/1000)}{(1 - w/1000)}$$  EQUATION 27 either air stream whether a net carbon dioxide flux is present or not, an apparent carbon dioxide mole fraction difference develops. This dilution effect can be corrected to the water vapor mole fraction that is in the reference air stream with equation 27 where $C_s^{ws}$ is the actual $CO_2$ mole fraction in the sample cell diluted by $W_s$ and $C_s^{wr}$ in the equivalent sample cell carbon dioxide mole fraction if it were diluted by $W_{ref}$.

In FIG. 5, there is shown a schematic circuit diagram of the automatic gain control amplifier 120 having first, second, third, and fourth operational amplifiers 200, 202, 204 and 206. The first and second operational amplifiers 200 and 202 are electrically connected in series between input conductor 112 receiving signals from the water vapor detector and a conductor 132 connecting the automatic gain control amplifier 120 to the subtractor 126 (FIG. 3). The input conductor 110 is electrically connected to the noninverting terminal of the operation amplifier 200 through the 0.0047 microfared capacitor 208, with the noninverting terminal being connected to AC ground through a 20 megaohm resistor 210. The output terminal of the amplifier 200 is electrically connected to the noninverting input terminal of the amplifier 202 through a 0.47 microfarad capacitor 212 and is electrically connected to its inverting input terminal through a 0.001 microfarad capacitor 214 and to its output terminal through a 2.21 kolohm resistor 216, forming an RC circuit. A noninverting input terminal of the amplifier 202 is electrically connected to a ground through a 2.21 kilohm resistor 217.

With this arrangement, sample and reference signals are periodically applied to conductor 112 as a series of chopped pulses. The amplifier 200 acts as an automatic gain control amplifier under the control of the remainder of the circuitry which has a time constant much higher than the clock pulses which switch the signal from a reference signal to a sample signal in synchronism with the chopper wheel 62 (FIG. 2) and the light openings applied through the sample flow cell 70 and reference flow cell 72 (FIG. 2).

To adjust the gain of amplifier 200, amplifiers 204 and 206 are in circuit with four N type field effect transistors 220, 222, 224 and 226 and are electrically connected in series with each other between the output conductor 132 and field effect transistor 226 that controls the gain of amplifier 200. The noninverting input terminal of the amplifier 204 is electrically connected to conductor 236 through the 0.22 microfarad capacitor 216 to receive signals from conductor 132 and to ground through the field effect transistor 220 and a 22 kilohm resistor 230. The field effect transistor is electrically connected to receive clock pulses on cable 65 to connect the resistor 230 to ground or block it from ground so that the noninverting input terminal of the amplifier 204 receives a signal from conductor 132 when it represents the reference value but not when it represents the signal value.

The output of amplifier 204 is electrically connected to its inverting input terminal and to the sources of field effect transistors 222 and 224 through a one megaohm resistor 232. The drain of the field effect transistor 222 is grounded and its gate is electrically connected to receive clock pulses. Similarly, the gate of the field effect transistor 224 is electrically connected to receive synchronizing pulses from cable 65 and its drain is electrically connected to the inverting terminal of the operational amplifier 206 which is electrically connected as an integrator with a 0.47 microfarad feedback capacitor 234.

A source of a −14 volts 124 is electrically connected to the source electrode of the field effect transistor 224 through a 2 megaohm resistor 238. The output of the amplifier 206 is electrically connected to the gain control circuit which includes a 33K resistor 240, a 470 kilohm resistor 242 and a 470 kilohm resistor 244 electrically connected in series in the order named between the output of the amplifier 206 and the gate electrode of the field effect transistor 226. A forward biased 1N4148 diode 246 and a 10 kilohm resistor 248 are electrically connected in parallel between the resistors 240 and 242 and ground and 0.1 microfarad capacitor 250 is electrically connected between the resistors 224 and 242 and ground.

The source and drain electrodes of the field effect transistor 226 are electrically connected to each other through two 100 ohm resistors 252 and 254, with the drain of the field effect transistor 226 being grounded and the source being electrically connected to the inverting input terminal of the amplifier 200 to control its gain. The midpoint between the resistors 252 and 254 is electrically connected back to the gate electrode of the field effect transistor 226 through a 0.1 microfarad capacitor 256.

This circuit in many respects acts as a synchronous demodulator to discriminate against noise while at the same time controlling the application of the reference voltage to the automatic gain control amplifier to continually adjust the gain of that amplifier so as to maintain the reference signal constant and to apply the scaling factor that accomplishes this to the sample voltage at conductor 132.

Figure 6:
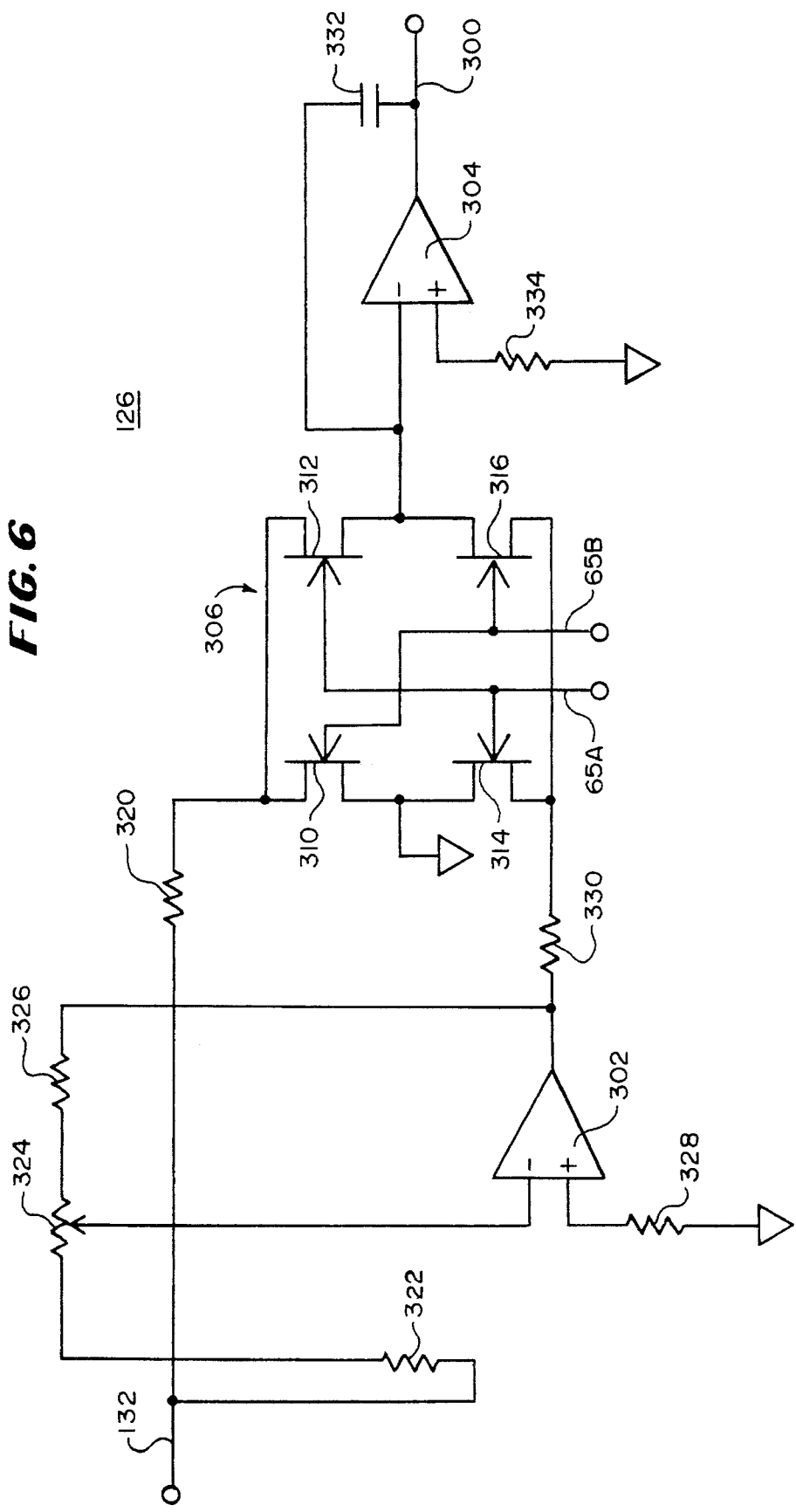
FIG. 6 is a schematic circuit diagram of another portion of the interface circuit of FIG. 3.

In FIG. 6, there is shown a schematic circuit diagram of the subtractor 126 for receiving sample signals and reference signals on conductor 132 and applying their difference to conductor 300, having a first operational amplifier 302, a second operational amplifier 304 and a field effect transistor bridge 306. The output terminal 300 of the integrating amplifier circuit 304 provides the difference between the sample signal and a reference signal.

The input amplifier circuit 302 is connected to the input to receive a portion of the sample and reference signals and apply them to the bridge circuit 306. Input terminal 132 is also connected to the opposite side of the bridge. The bridge 306 includes four field effect transistors connected to receiving timing pulses from the timing signal detector 63 (FIG. 1) in response to rotation of the chopper wheel 62 (FIG. 2) through different conductors of the cable 65. These pulses are spaced to alternately apply the inverted reference signal and the sample signal to the inegrating operational amplifier 304 for the subtraction of the reference signal from the sample signal.

For this purpose, the bridge circuit 306 includes four N type field effect transistors 310, 312, 314 and 316. Input terminal 132 is electrically connected: (1) through a 33.2 kilohm resistor 320 to the source of the field effect transistor 310 and to the drain of the field effect transistor 312; and (2) to the output of the amplifier 302 through a 33.2K resistor 322, a 1 kilohm potentiometer 324 and a 33.2 kilohm resistor 326 in the order named. The tap of the potentiometer 324 is electrically connected to the inverting terminal of the amplifier 302, with its noninverting input terminal being electrically connected to ground through a 10K resistor 328. The output of the amplifier 302 is electrically connected to the source of the field effect transistor 314 and to the drain of the field effect transistor 316 through a 33.2K resistor 330.

The gate electrodes of the transistors 314 and 312 are electrically connected to one conductor 65A of the cable 65 and the gate electrodes of the transistors 310 and 312 are electrically connected to another conductor 65B of the cable 65 so that these two pairs of field effect transistors are alternately energized in accordance with timing pulses to apply reference and sample signals. The drains of the transistors 310 and 314 are grounded and the sources of the transistors 312 and 316 are electrically connnected to the inverting input terminal of the amplifier 304, which inverting input terminal is electrically connected to the output conductor 300 through the 0.47 microfarad capacitor 332. The noninverting terminal of the amplifier 304 is grounded through a 1K resistor 334 to permit the combining of the inverted and noninverted reference and sample signals and apply them to the terminal 300.

Figure 7:
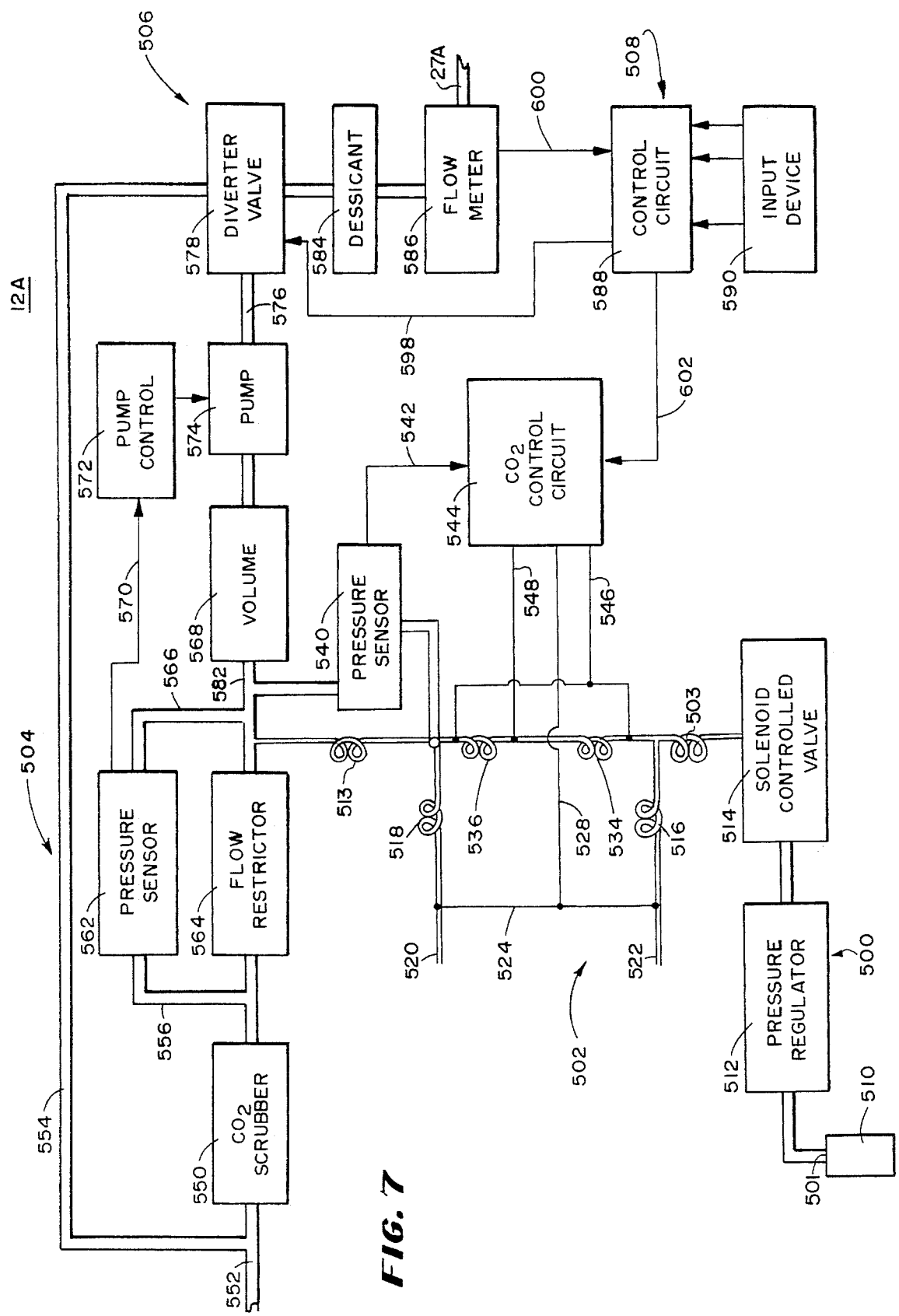
FIG. 7 is a block diagram of a system for supplying gas to a gas analyzer in accordance with an embodiment of the invention.

In FIG. 7, there is shown a block diagram of an open path gas source 12A which may be used instead of the source shown generally at 12 in FIG. 1 having a carbon dioxide source 500, a carbon dioxide flow rate control system 502, an open path gas source 504 and a gas control system 506. The carbon dioxide source 500 includes a coupling connection 501, a pressure regulator 512 and a solenoid controlled valve 514. The coupling 501 is adapted to be removably connected to a small pressurized carbon dioxide source 510 for communication with the pressure regulator 512 such as by screw threads. The solenoid controlled valve 514 is electrically connected to the input device 590 to open and close the valve 514 and pneumatically connected to the pressure regulator 512 to receive carbon dioxide for supplying to a capillary tube 503.

To control the flow of carbon dioxide, the carbon dioxide flow rate control system 502 includes the first capillary tube restrictor 503, a second capillary tube restrictor 516, a third capillary tube restrictor 534, a fourth capillary tube restrictor 536, a fifth capillary tube restrictor 518, a sixth capillary tube restrictor 513 and a carbon dioxide electrical control circuit 544.

To permit the flow of carbon dioxide to the open path gas source, one end of the capillary tube restrictor 503 communicates with the pressure regulator 512 through the solenoid controlled valve 514 when the solenoid-controlled valve 514 is opened by a signal from the input device 590. The other end of the capillary tube restrictor 503 communicates with a first end of the second capillary tube restrictor 516 and a first end of the third capillary tube restrictor 534, with the other end of the second capillary tube restrictor 516 communicating with the exhaust port 522. The other end of the third capillary tube restrictor 534 communicates with the fourth capillary tube restrictor 536.

To control the rate of flow of carbon dioxide, the carbon dioxide control circuit 544 is electrically connected: (1) between the capillary tube restrictors 534 and 536 by conductor 548; (2) between capillary tube restrictors 503, 516 and 534 by conductor 546; (3) between capillary tube restrictors 536, 518 and 513 by conductor 546; (4) between capillary tube restrictor 518 and exhaust port 520 by conductor 528; and (5) between exhaust port 522 and capillary tube restrictor 516 by conductor 528. The capillary tube restrictors have high resistant coats on them so that the flow of electricity heats the capillary tubes, increasing the viscosity of the gas in them and slowing the rate of flow. These conductors and capillary tube restrictors form an electrically controllable pneumatic bridge for the flow of carbon dioxide from the solenoid valve 514 through the open path gas source 504 to the volume 568. To increase the dynamic range of the carbon dioxide flow rate control system 502, the second capillary tube restrictor 516 communicates with the atmosphere at port 522 and the fifth capillary tube restrictor 518 communicates with the atmosphere at each port 520.

To control the flow, capillary tube restrictors 503, 534, 536 and 513 are connected in series and form a flow path from the source of carbon dioxide and to the volume 568. Capillary tube restrictors 516 and 518 are shunt flow restictors that exhaust through ports 522 and 520 and thus reduce the flow through capillary tube restrictors 503, 534, 536 and 513. The series capillary restrictors 534 and 536 are connected in parallel with electrical conductors 546 and 548 so that electric current flowing through conductors 548 and 546 causes Joule heating of the series-connected capillary tube restrictors 534 and 536 because of their electrical resistance and shunt capillary restrictors 516 and 518 are connected in parallel with electrical conductors 546 and 528 so that electric current flowing through conductors 546 and 528 and through the resistance of the capillary tubes causes Joule heating of the shunt capillaries 518 and 546.

Since the flow restriction capillaries are small in diameter and flow rates are low, the flow distribution inside the capillary is laminer. In laminer flow conditions, the flow rate is inversely proportional to the viscosity of the gas. Since the viscosity of a gas is somewhat temperature dependent, temp changes can effect a change in the flow rate of gas through the restriction capillaries.

To increase the range of flow control, several techniques are employed such as for example: (1) a large temperature excursion is used (greater than 200 degrees centigrade) because the viscosity dependence of gas with temperature is small; (2) a series and shunt configuration multiplies the range of control at the expense of wasting a portion of the gas; (3) the temperature excursion of the series and shunt restrictors are inversely coupled so that when one group heats, the other group is allowed to cool in the same proportion and vice versa; and (4) the flow of carbon dioxide is sensed by the pressure drop across flow restriction capillary 513 and solid state pressure sensor 540. The signal from 540 feeds the carbon dioxide control circuit 544 which controls the temperature of the series, and shunt capillaries and regulation of small flow rates of carbon dioxide is accomplished.

With this arrangement, carbon dioxide is applied through the sixth capillary tube restrictor 513 from the bridge to the open path gas source 504 in selected amounts to control the carbon dioxide content of air when desired. The volume of air and carbon dioxide being supplied is sensed by a pressure sensor 540 which applies signals through conductor 542 to the carbon dioxide control circuit 544 .for controlling the heat applied to the bridge and thus the amount of carbon dioxide flowing to the open path gas source 504.

To supply gas from atmospheric air, the open path gas source 504 includes an inlet vent conduit 552, a bypass conduit 554, a pressure sensor 562, a flow restrictor 564, a volume tank 568, a pump control circuit 572 and a pump 574. The conduit 552 communicates directly with the gas control system 506 through: (1) the conduit 554; (2) a carbon dioxide scrubber 550; (3) the flow restrictor 564; (4) the volume pressure stabilizer; and (5) the pump 574 in the order named.

The pressure sensor 562 communicates through a conduit 556 with the scrubber 550 and the flow restrictor 564 and with a conduit 566 to the conduit 582 to measure the pressure across the flow restrictor 564. This signal is applied through conductor 570 to the pump control circuit 572 which controls the pump 574 to pump at a rate that maintains the pressure and the flow restrictor 564 constant into the gas control system 506.

In the preferred embodiment, the restrictor 503 is four inches long, receives an inlet pressure of 50 psi (pounds per square inch) and has a diameter of 0.004. (4 thousandths) inch. The heaters on capillary 524 and between restrictors 534 and 536 increase the temperature up to 250 degrees Centigrade. The maximum air flow into the volume 568 is two cubic centimeters per minute and the sensors 540 and 562 are solid state pressure transducers.

To supply the final mixture of gases to tube 27A for connection to the analyzer cells or the plant chamber 20 (FIG. 1), the gas processing system 506 includes a diverter valve 578, a dessicant tube 584, a flow meter 586 and the conduit 27A. The conduit 27A is similar to the conduit 27 shown in the embodiment of FIG. i and is thus connectable by two switches 22 and 29 to the plant chamber 20 or the sample cell 34 or reference cell 36 or variations of the sample cell and reference cell to be described hereinafter. The switching system need not include the gas processing section 26 shown in the embodiment of FIG. 1, but otherwise the switching system including switches 22 and 29 of FIG. 1 is suitable.

The diverter valve 578 to be described in greater detail hereinafter receives gas from the conduit 576 pumped by the pump 574 as selected by a two-way solenoid valve 514 under the control of the control circuit 588. This diverter valve 578 can be adjusted in a manner described hereinafter to pump all or any portion of the gas on conduit 576 to dessicant chamber 584 and to recirculate the rest through conduit 554 under the control of a signal on conductor 598 for passage through the dessicant 584 and the flow meter 586 before being applied through conduit 27A. The flow meter 586 is electrically connected to the control circuit 508 through conductor 600 to control the amount of carbon dioxide under the control of the input device 590 in the gas control system 506.

To supply the proper proportion of gases, the control circuit 508 is connected to: (1)the input device 590 for recording the amount of carbon dioxide as indicated through conductor 602 to the carbon dioxide control circuit 544; and (2) the diverter valve 578 through conductor 598 to supply the proportionate. mixture of gases as supplied by the diverter valve 578 through conduit 27A. With this arrangement, the flow of gas can be controlled by control circuit 508 as entered into input device 590.

In FIG. 8, there is shown a fragmentary sectional view of the diverter valve 578 having a gas inlet port 612 adapted to communicate with the conduit 576 (FIG. 7), a first outlet port 624 adapted to communicate with the conduit 554 (FIG. 7) for recirculation and a second outlet port 622 communicating with the dessicant 584. Gases from the inlet port 612 are proportioned by the diverter valve 578 for application to an outlet port to the dessicant or for recirculation.

To control the ratio of gases recirculated and applied to conduit 27A, the valve 578. includes a cylindrical bottom body portion 620 having a centrally located inlet port 612, the first outlet port 624 and the second outlet port 622, a control disk 616, a top portion of the body 610, and a motor driven shaft 614. The position of the control disk or plate 616 is controlled by the control circuit 588 (FIG. 7) which serves as a means that positions the disk or plate 616 to properly proportion the flow of gases collected by outlet grooves 626 and 628, and exiting through ports 622 and 624 and thus serves as a means for positioning the control disk.

The bottom body portion 620 is cylindrical with the inlet port 612 being centered and first and second grooves 626 and 628 (FIG. 9) being formed in its surface. The outlet port 622 passes through the first groove 626 and the outlet port 624 passes through the other groove 628. With this arrangement, the gas entering the inlet port 612: (1) flows more readily toward the groove 626 when the area between the inlet hole 612 and the outlet groove 626 is exposed to a greater extent; and (2) flows more readily to the groove 628 when the area between the inlet hole 612 and the outlet groove 628 is exposed to a greater extent.

To control the proportion of gas recirculated and the proportion pumped to conduit 27A by controlling the position of disk 616, the control disk 616 (FIG. 10) is fitted for movement with the motor driven shaft 614 by the motor 615. This motor positions the disk 616 to cover more or less of the area leading to collection grooves 626 and 628. It may entirely block all flow to one groove and fully open the path leading to the other groove, or be positioned somewhere between these two locations. This proportioning of flow results from the very close tolerance between plate 616 and upper plate 610 and lower plate 620. This diverter valve may also be used as a split flow input at the junction of the seventh restrictor 513 or the inlet of the flow restrictor 503 to provide split flow injection of carbon dioxide.

In FIGS. 11 and 12, there is shown a sectional view of one embodiment of analyzer 14A which may be used as a substitute for the analyzer 14 of FIG. 2 having two gas sensing chambers 70A and 72A, only the sensing chamber 72A being shown in FIG. 11 and a housing 650 for the optics and electronic portion. The chambers 72A and 70A are analogous to the chambers 70 and 72 of FIG. 2.

As shown in FIG. 11, the chamber 70A includes a light path passing through the lens 672. and window upwardly to a mirror 668 which reflects it to a mirror 666 at an opposite corner. The mirrors 668 and 666 are at 45 degrees so that a beam is reflected downwardly parallel to the upwardly moving beam from the lens 672 to the lens 671 for sensing in the housing 650. The cell 72A is adapted to be filled with a gas through a port 673 at the bottom of the chamber for flow to an upper port 675, the light absorbance of which is to be be sensed.

To supply light through the cell, the housing 650 includes a light source 674, mounted for control to a circuit board for energization thereof, a tubular channel leading to a lens 672 and window sealed by O-rings to provide gas integrity of the gas in the chamber 72A. At the opposite side of the chamber housing, the lens 671 is mounted to receive light passing through the gas in the chamber 72A and transmit it through a filter disk 656 positioned to select the desired frequency onto a photodetector 658. The filter disk 656 is rotatably driven so as to position the filter section before the photodetector in a manner known in the art. Peltier cells 662 and 664 maintain the temperature of the photodetector 658 constant.

In FIG. 12, there is shown a transverse sectional view of the analyzer 14A having first and second gas cells 70A and 72A including respective mirrors 666 and 667 and being separated by dividing wall 669, each being adapted to receive gas and having its own separate detection system and light source as shown in FIG. 11. However, a single light source can be used as shown in the embodiment of FIG. 2. As best shown in the embodiment of FIG. 12, the chopper housing includes chopper disk 656 which serves a chopper for both detectors 658 and 660 to process the light entering from either of the gas cells 70A and 72A driven by the motor 654.

From the above description, it can be understood that the analyzing instrument of this invention has several advantages, such as: (1) it provides relatively precise measurements; (2) it is possible to measure both water vapor and carbon dioxide in the same mixture at the same time without introducing excessive errors because of second order effects due to band broadening of the gases; (3) it is relatively fast in operation because it only requires measurements of the same gas; (4) it is less complicated because it does not require measurement of carbon dioxide in dry air after water vapor has been removed from it; and (5) it is relatively inexpensive.

Although a preferred embodiment of the invention has been described with some particularity, many modifications and variations in the invention are possible within the light of the above teachings. Therefore, it is to be understood that, within the scope of the appended claims, the invention may be practiced other than as specifically described.

What is claimed is:

1. A gas analyzing system, comprising:

first and second light sources;

a reference flow cell and a sample flow cell;

first and second detecting means for detecting light transmitted from a corresponding one of said first and second light sources through said reference flow cell and through said sample flow cell and generating first and second signals representing each of said light transmitted through said reference flow cell and light transmitted through said sample flow cell;

means for receiving said reference and sample signals;

said reference and sample flow cells each including a plurality of mirrors wherein light is reflected through multiple paths in said reference and sample flow cells;

means for supplying carbon dioxide through a capillary restrictor tube;

means for heating the tube to change the viscosity of the carbon dioxide wherein the flow rate of the carbon dioxide is controlled; and means for supplying the carbon dioxide to a diverter valve, wherein a selected proportion of the carbon dioxide is diverted and the remainder applied to the gas analyzing system.

\* \* \* \* \*